United States Patent [19]

Schwarz et al.

[11] Patent Number: 5,150,617
[45] Date of Patent: Sep. 29, 1992

[54] MAGNETOSTRICTIVE RESONANCE EXCITATION

[75] Inventors: Ricardo B. Schwarz, Los Alamos, N. Mex.; Veli-Tapani Kuokkala, Tampere, Finland

[73] Assignee: The United States of America as represented by the United States Department of Energy, Washington, D.C.

[21] Appl. No.: 574,404

[22] Filed: Aug. 29, 1990

[51] Int. Cl.⁵ .......................................... G01N 29/12
[52] U.S. Cl. ........................................................ 73/579
[58] Field of Search ................ 73/579, 599, 643, 644, 73/571, 576

[56] References Cited

U.S. PATENT DOCUMENTS

| | | | |
|---|---|---|---|
| 3,308,650 | 3/1967 | Fitzgerald | 73/571 |
| 4,879,905 | 11/1989 | Chen et al. | 73/579 |
| 4,924,706 | 5/1990 | Moore | 73/579 |
| 4,976,148 | 12/1990 | Migliori et al. | 73/579 |

OTHER PUBLICATIONS

H. H. Demarest, Jr., "Cube-Resonance Method to Determine the Elasti Constants of Solids," 49 J. Acout. Soc. Amer., No. 3, Part 2, pp. 768 (1971).

E. Schreiber et al., "Resonant-Sphere Methods for Measuring the Velocity of Sound," *Elastic Constants and Their Measurement*, McGraw-Hill, 1974.

I. Ohno, "Free Vibration of a Rectangular Parallelepiped Crystal and Its Application to Determination of Elastic Constants of Orthorhombic Crystals," 24 J. Phys. Earth, pp. 355 (1976).

K. Kakuno et al., "A New Measuring Method of Magnetostrictive Vibration," 50, J. Appl. Phys., No. 80, pp. 7713 (1979).

*Primary Examiner*—Hezron E. Williams
*Assistant Examiner*—Louis M. Arana
*Attorney, Agent, or Firm*—Ray G. Wilson; Paul D. Gaetjens; William R. Moser

[57] ABSTRACT

The resonance frequency spectrum of a magnetostrictive sample is remotely determined by exciting the magnetostrictive property with an oscillating magnetic field. The permeability of a magnetostrictive material and concomitant coupling with a detection coil varies with the strain in the material whereby resonance responses of the sample can be readily detected. A suitable sample may be a magnetostrictive material or some other material having at least one side coated with a magnetostrictive material. When the sample is a suitable shape, i.e., a cube, rectangular parallelepiped, solid sphere or spherical shell, the elastic moduli or the material can be analytically determined from the measured resonance frequency spectrum. No mechanical transducers are required and the sample excitation is obtained without contact with the sample, leading to highly reproducible results and a measurement capability over a wide temperature range, e.g. from liquid nitrogen temperature to the Curie temperature of the magnetostrictive material.

10 Claims, 4 Drawing Sheets

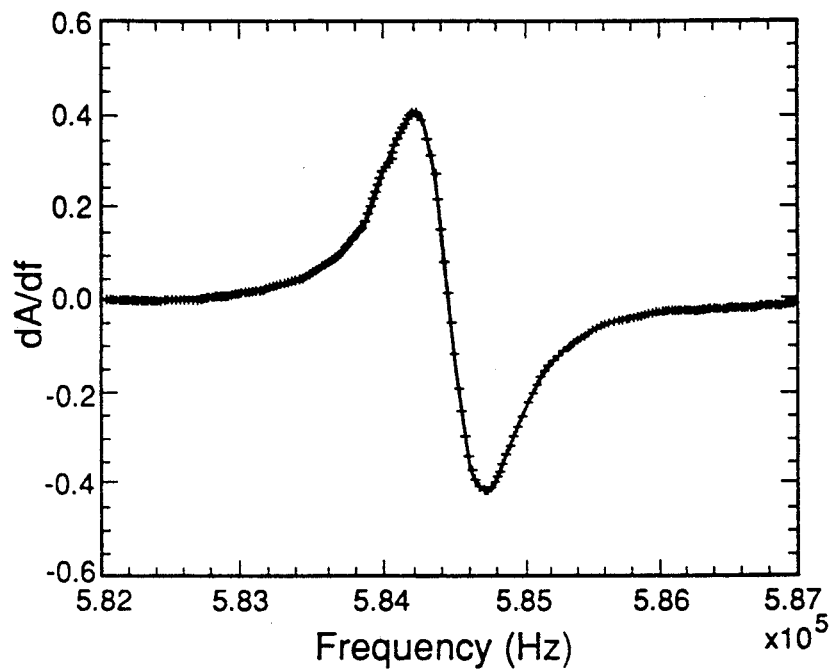
Fig. 6
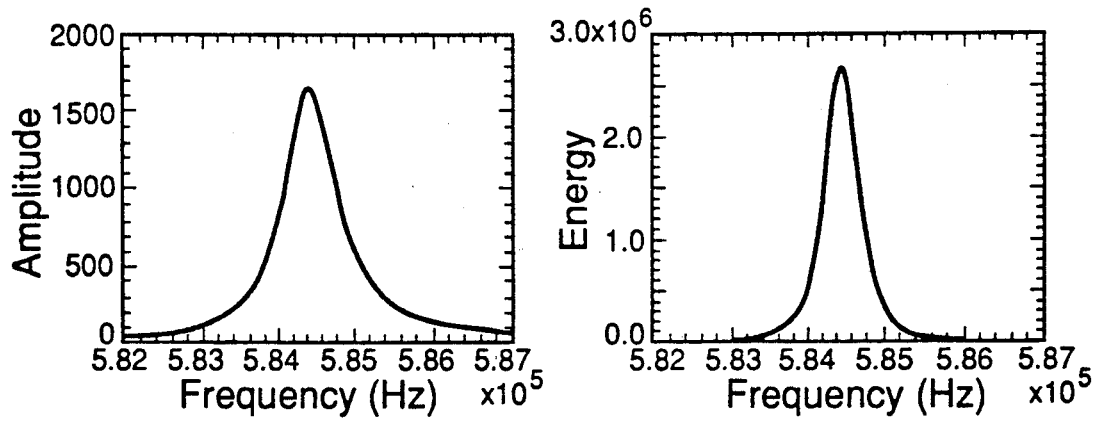
Fig. 7a     Fig. 7b

MAGNETOSTRICTIVE RESONANCE EXCITATION

BACKGROUND OF INVENTION

This invention relates to the determination of the elastic moduli and ultrasonic attenuation of materials and, more particularly, to the determination of elastic moduli and ultrasonic attenuation by sample resonant frequency excitation. This invention is the result of a contract with the Department of Energy (Contract No. W-7405-ENG-36).

The elastic properties of solid materials, described by their elastic moduli, are of great technological and scientific interest. The elastic moduli simply relate linear, reversible strains in the material to the applied (external) stresses. The elastic moduli also contain important information about the forces between individual atoms in different three-dimensional configurations, i.e., in different periodical crystal lattices and in the more or less random and disordered arrangements of atoms found in amorphous or glassy solids. The elastic moduli are basic physical parameters which give a direct link between macroscopic material properties and the atomic level structure of the material.

In the most general case, 36 independent elastic moduli are needed to fully describe the elastic stress-strain relationships in solid materials. In practice, however, different types of symmetries reduce the required number of elastic moduli considerably and, in the case of cubic single crystals, only three independent moduli are needed. Furthermore, in isotropic (non-textured) materials and amorphous solid materials, the number of independent elastic moduli is reduced by one, leaving only two elastic moduli to be determined experimentally.

The most common methods employed to determine elastic moduli are based on the measurement of sound velocities. In the standard resonance methods for measuring sound velocities, a rectangular or cylindrical sample, having one relatively large dimension, is excited for flexural, torsional, or longitudinal vibration, the mode of vibration determining the type of elastic modulus to be measured. With this method, usually only one elastic modulus is determined for each sample and measurement.

For samples other than long rods or thin reeds, i.e., samples with comparable dimensions, these simple techniques are not useful because there is no known analytical relationship that allows the elastic moduli to be deduced from the measured mechanical resonance frequencies. For some simple solid shapes, such as spheres, spherical shells, cubes and rectangular parallelepipeds, analytical methods have been developed to calculate the spectrum of mechanical resonance frequencies from a set of assumed elastic moduli. Then, a comparison of the calculated and measured spectra allows the indirect determination of the sample's elastic moduli.

A resonant sphere technique developed by Fraser and LeCraw, and described by E. Schreiber et al., "Resonant-Sphere Methods for Measuring the Velocity of Sound," *Elastic Constants and Their Measurement*, McGraw-Hill, 1974, is applicable only to homogeneous and isotropic materials. The three elastic constants of a cube-shaped cubic single crystal can be determined as described in H. H. Demarest, Jr., "Cube-Resonance Method to Determine the Elastic Constants of Solids," 49 J. Acoust. Soc. Amer., No. 3, Part 2, pp. 768 (1971). This technique was extended to rectangular parallelepiped samples with orthorhombic crystal symmetry and nine independent elastic constants by I. Ohno, "Free Vibration of a Rectangular Parallelepiped Crystal and Its Application to Determination of Elastic Constants of Orthorhombic Crystals," 24 J. Phys. Earth, pp. 355 (1976). In all of these resonance techniques, a sample is lightly clamped between two piezoelectric transducers for excitation and detection of the sample response. A maximum response is detected when the excitation frequency coincides with any resonant frequency of the sample.

In this rectangular parallelepiped resonance (RPR) method, the determination of elastic constants is based on the matching of theoretically calculated and experimentally measured resonance spectra. A resonance spectrum is calculated starting from the known dimensions and density of the sample and from the estimated values of a known set of elastic constants of the material forming the sample. A trial and error technique for determining the sample constants is described in U.S. Pat. No. 4,976,148, "Resonant Ultrasound Spectrometer," filed Sep. 12, 1989, incorporated herein by reference.

One problem with the RPR technique is that transducer contact with the sample can alter the detected resonance spectra and introduce harmonic resonances into the spectra. Another limitation to high-temperature measurements arises from the glues and epoxies used to hold the piezoelectric transducers in the apparatus. Another problem is that piezoelectric transducers are not operable at high temperatures and high temperature data cannot be obtained. One other problem is that samples cannot easily be removed and replaced in the clamping device with reproducible results. These and other problems in the prior art are overcome by the present invention wherein magnetostriction is employed to remotely excite a sample and detect the sample response.

Accordingly, one object of the present invention is to provide an excitation and response detection system for operating at high sample temperatures.

Another object of the present invention is to remotely excite a sample through an excitation frequency range and detect the resonant responses.

One other object is to eliminate the introduction of sample holder resonances into the sample resonance spectrum.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise a system for remotely determining the resonant spectrum of a material sample for use in calculating the material elastic moduli using the RPR method. A material sample having magnetostrictive properties is placed within an exciting coil for producing an oscillating magnetic field over a frequency range selected to include sample resonant frequencies. A detection coil is placed about the sample to detect the sample response to the exciting magnetic field. In particular embodiments, the sample material may be a ferromagnetic, magnetostrictive material, or the sample material may be coated on one or more sides with a ferromagnetic, magnetostrictive material.

In another characterization of the present invention a method is provided for determining the resonant frequency spectrum of a material for use in calculating the elastic moduli of the material using the RPR method. The material sample is formed with magnetostrictive characteristics and placed inside a sample exciting coil. The coil is energized with an oscillating signal over a frequency range corresponding to expected resonances in the sample. The sample response to the exciting magnetic field produced by the exciting coil is detected by a detection coil adjacent the sample wherein the sample resonant frequency spectrum is developed.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings:

FIG. 6 graphically depicts the measured output from a lock-in amplifier depicted in FIG. 3 and a smooth curve fit to the data.

FIGS. 7A and 7B graphically depict a resonance peak amplitude deconvoluted from the output shown in FIG. 6 and corresponding energy curve.

DETAILED DESCRIPTION OF THE DRAWINGS

A magnetostrictive resonator system measures the resonances of a material sample. The sample may be of any shape or form for which computational methods allow the computation of the spectrum of resonance frequencies. The sample is preferably formed as a cube, rectangular parallelepiped, solid sphere, or spherical shell. A magnetostrictive thin film is deposited on at least one surface of the sample and an applied magnetic field causes the film to perform as a magneto-mechanical vibrator to excite the sample into mechanical vibrations. The magnetostrictive film also acts as a transducer for the detection of mechanical resonances of the sample. The size of the sample is not critical. Samples of millimeter size are preferred since they are relatively easy to manufacture and have resonances above about 200 KHz.

A spectrum of resonance frequencies is measured by sweeping the frequency of the applied magnetic field over a selected range while keeping the temperature constant at some arbitrary value $T_o$. The ultrasonic attenuation for each resonance is then deduced from the measured dependence of the amplitude on frequency near the resonance. A complete set of elastic moduli and the ultrasonic attenuation can be measured on a single sample over a wide temperature range extending from cryogenic temperatures to the Curie temperature of the magnetostrictive film.

Figure 1:
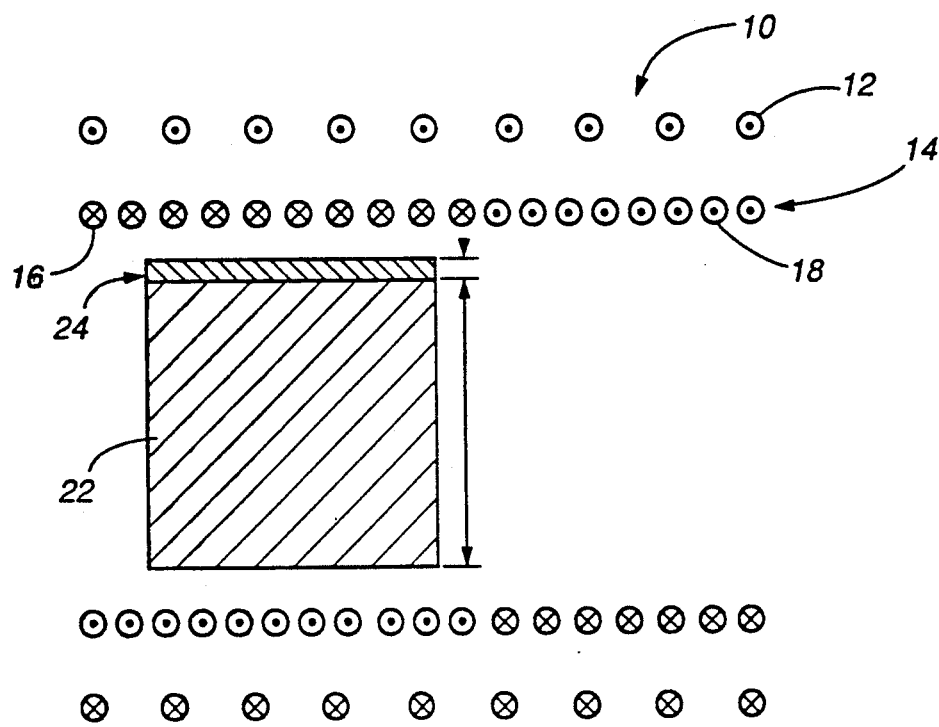
FIG. 1 is a schematic illustration of the magnetostrictive resonance excitation scheme according to one embodiment of the present invention.

Referring now to FIG. 1, there is schematically shown a magnetostrictive resonance excitation apparatus 10 according to the present invention. Excitation solenoid 12 is formed coaxial with signal detection solenoid 14. Signal solenoid 14 is preferably formed with coils 16 and 18 wound in opposite directions, wherein solenoid 14 can be positioned coaxially within excitation solenoid 12 to provide a minimum output signal in the absence of any sample material. Sample material 22 has magnetostrictive properties and may be ferromagnetic or may be a non-ferromagnetic material coated on at least one side with a magnetostrictive material film 24, e.g. nickel, cobalt-iron alloy, etc. As used herein, it will be assumed that the magnetrostrictive properties are from a filmed sample, but it will also be apparent that the properties may arise from a magnetostrictive substrate itself with no additional film.

Figure 2:
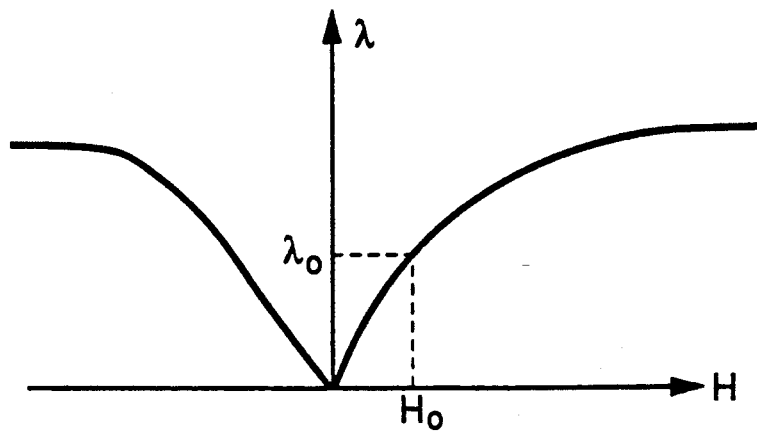
FIG. 2 graphically illustrates the magnetostrictive constant of nickel as a function of applied magnetic field.

Magnetostrictive film 24 acts both as a driving and a detecting transducer. As a drive transducer, film 24 is responsive to an applied magnetic field and generates stresses in the sample at a frequency that drives the sample into mechanical resonance. As a detection transducer, film 24 undergoes strain-induced changes in its magnetic permeability, determined by the vibrational state of the sample, that produce a corresponding change in the output from detection solenoid 14. FIG. 2 graphically illustrates the magnetostrictive constant $\lambda$ of film 24 as a function of magnetic field H. To generate a stress $\sigma(\omega t)$ of the same frequency $\omega$ as the signal applied to solenoid 12, the magnetic field, H, must be biased to provide an operating region along the linear portion of the characteristic curve shown in FIG. 2. This can be conventionally done by (a) applying an external magnetic field $H_o$ with a permanent magnet; (b) applying field $H_o$ by passing a DC current through solenoid 14; or (c) magnetizing the magnetostrictive film itself.

The relationship between the applied magnetic field $H(\omega t)$, the magnetic induction in the film B, the longitudinal stress $\sigma$, and the longitudinal strain $\epsilon$, are described by conventional linear equations. See, for example, E. Olsen, *Applied Magnetism, A Study in Quantities*, Chapter 11, Springer Verlag, New York, 1966. When the frequency $\omega$ is away from a mechanical resonance of sample 22, the sample is still and the magnetostrictive film is essentially clamped or $\epsilon = 0$. The stress applied to sample 22 by film 24 can then be shown to be $$\sigma = -eH,$$

where $e = -(\partial\sigma/\partial H)_\epsilon$ is the magneto-elastic coefficient at constant strain. The magnetic induction away from resonance is $$B^\epsilon = \mu^\epsilon H,$$

where $\mu^\epsilon$ is the film permeability at constant strain.

Looking now at the relationships when sample 22 is resonating mechanically, the mechanical losses in sample 22 are assumed to be negligibly small (high Q-factor), where the film has to do little work in maintaining these resonances. Thus, as a first approximation, film 24 can be considered uncoupled from sample 22 and vibrating freely, i.e., no stress in film 24. The magnetic induction at resonance can then be written as $$B^\sigma = \mu^\sigma H,$$

where $\mu^\sigma$ is the film permeability at constant stress. In magnetostrictive materials, $\mu^\sigma > \mu^\epsilon$, i.e., film 24 has a higher permeability when sample 22 is resonating mechanically and magnetostrictive film 24 deforms elastically in phase with the frequency.

The permeability of film 24 contributes to the mutual inductance between excitation solenoid 12 and detection solenoid 14. A signal $V_2(\omega t + \Phi)$ detected by detection solenoid 14 will increase at the mechanical resonance of sample 22. The increase in $V_2$ caused by changes in the permeability in film 24 is proportional to $$\frac{B^\sigma - B^\epsilon}{B^\epsilon} = \frac{\mu^\sigma - \mu^\epsilon}{\mu^\epsilon} = \frac{k^2}{1 - k^2} = R,$$

where k is the magneto-mechanical coupling coefficient. For film 24 of nickel, $k \approx 0.31$ which gives $R = 0.11$, an 11% increase in film 24 contribution to the mutual inductance. The use of a thin film material with a higher k value, such as Terfenol-D ™, would give still higher R values, i.e. $R = 1.08$ with $k = 0.72$.

Figure 3:
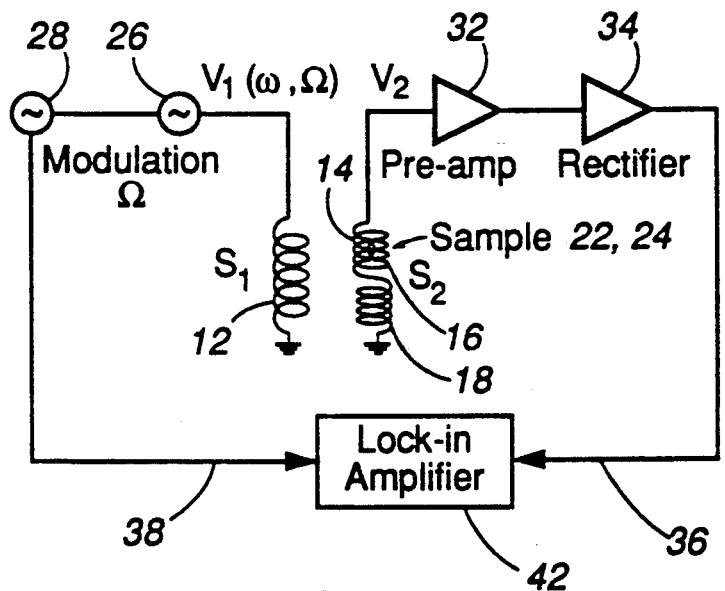
FIG. 3 is a schematic of a system for measuring the mechanical resonance spectrum of a sample using magnetostrictive excitation and detection of the sample vibrations.

It will be appreciated that thin film 24 makes only a small contribution to the total mutual inductance between excitation solenoid 12 and detection solenoid 14 (FIG. 1) and the increase in output signal is significantly smaller than these R values. FIG. 3 schematically depicts an exemplary system for increasing the signal-to-noise ratio of the output signal $V_2$. Solenoid $S_2$ 14 is formed by two identical coils 16, 18, one wound clockwise and one wound counter-clockwise, and is placed coaxial within excitation solenoid 12. With filmed sample 22, 24 removed from the system, the position of $S_2$ 14 relative to $S_1$ 12 is adjusted to minimize the amplitude of $V_2$. When sample 22, 24 is placed within one of the coils 16, 18, the ratio $V_2/V_1$ is most sensitive to changes in the magnetic coupling provided by thin film 24. To further optimize the sensitivity, the position of sample 22, 24 is adjusted relative to coil $S_2$ for a maximum value of $V_2$.

Figure 4:
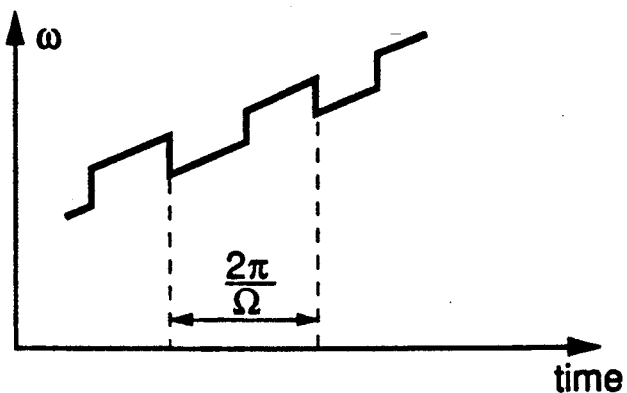
FIG. 4 is a graphical illustration of the excitation signal applied by the system shown in FIG. 3.

Function synthesizer 26 provides sinusoidal drive signal $V_1$ of frequency to excitation coil $S_1$ 12 and is phase modulated by modulator 28 with a triangular output signal $\Phi_1$ of frequency $\Omega$, $\Omega << \omega$. To measure the mechanical resonances of sample 22, 24, the frequency $\omega$ is swept in time. Thus, the driving signal is $$V_1 = V_{10} \cos(\omega t + \phi),$$

where $\omega$ increases slowly linearly with time and $\phi = \Phi_1(\Omega t)$. In effect, the excitation frequency alternates between two values with a periodicity $2\pi/\Omega$, as shown in FIG. 4, while the average frequency value increases linearly with time.

Signal $V_2$ from detector coil $S_2$ 14 is input through low-input capacitance pre-amplifier 32 to rectifier 34. Rectified signal 36 has an AC component of frequency $\Omega$ that is detected by lock-in amplifier 42, working at modulation frequency $\Omega$ from reference input 38. The system components hereinabove described are preferably controlled by a personal computer through an IEEE-448 standard interface (not shown).

Figure 5:
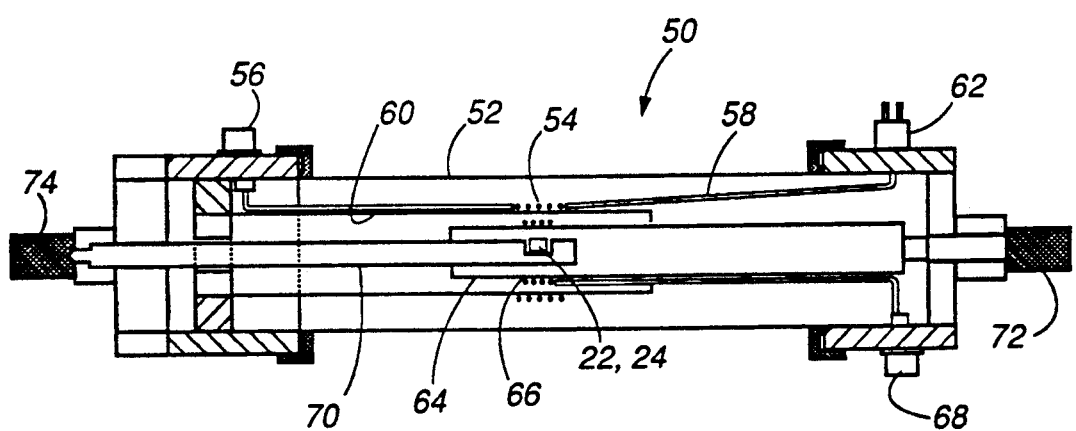
FIG. 5 is an illustration in partial cutaway of the mechanical arrangement of the sample holder used in the system shown in FIG. 3.

Referring now to FIG. 5, there is shown specimen holder assembly 50 for positioning sample 22, 24 and detection coil 66 coaxially within excitation coil 54. Outer shell 52 provides structural integrity for assembly 50, external electrical connections, and support for internal structure. Excitation coil 54 is wound about outer jacket wall 60 and connected by a coaxial cable to excitation signal connector 56. Thermocouple 58 provides an output signal through connector 62 indicative of the specimen temperature.

Detection coil 66 is wound on inner jacket wall 64 coaxial with outer jacket wall 60 and outputs a response signal through coaxial cable connector 68. Material sample 22 with magnetostrictive film 24 is carried in specimen holder 70. Micrometers 72 and 74 are connected to inner jacket wall 64 and specimen holder 70, respectively, for relatively moving detection coil 66 and specimen 22, 24 within excitation coil 54. Coils 54 and 66 are preferably of platinum wire and wound on fused silica tubes for high temperature operation. Outer shell 52 may be filled with an inert gas or may be evacuated. Assembly 50 may be placed in an external furnace for heating sample 22, 24 to obtain resonance data up to the Curie temperature of magnetostrictive film 24, or it may be cooled with a liquefied gas, such as nitrogen, for low operating temperatures, e.g., down to 90 K.

FIGS. 6-9 present exemplary results of the magnetostrictive resonance system discussed above. A sample was prepared of amorphous electrodeposited $Ni_{80}P_{20}$ alloy, formed to a rectangular parallelepiped of dimensions $1.832 \times 2.368 \times 3.170$ mm and density of 7.75 $g/cm^3$, coated electrolytically with pure nickel on three mutually perpendicular faces. The thickness of the nickel film varied between 15 and 18 $\mu$m, increasing the dimensions by about 0.75%.

FIG. 6 graphically illustrates a typical output from lock-in amplifier 42 (FIG. 3) as the frequency sweeps over a single mechanical resonance of the sample. Two quantities can be deduced from this data: the resonance frequency $\omega_r$ and the attenuation $Q^{-1}$. Assume that the resonance is described by a Lorentzian function, $$P(\omega) = \frac{A}{\pi} \frac{\Gamma/2}{(\omega - \omega_r)^2 + (\Gamma/2)^2}$$

of amplitude A, mean frequency $\omega_r$, and having a half-width $\Gamma$. The signal detected by the lock-in amplifier is the frequency derivative of $P(\omega)$, $$P'(\omega) = -\frac{A\Gamma}{\pi} \frac{\omega - \omega_r}{[(\omega - \omega_r)^2 + (\Gamma/2)^2]^2}$$

A numerical fit of this equation to the data in FIG. 6, shown as "+", enables parameters A, $\Gamma$, and $\omega_r$ to be deduced. If the background of the data is not zero over the range of frequencies swept in the measurements, the fit can be further improved by adding a linear term having the form $c_1 + c_2\omega$. As shown in FIG. 6, the fitted function describes very well the frequency derivative of the resonance peak.

Figure 8:
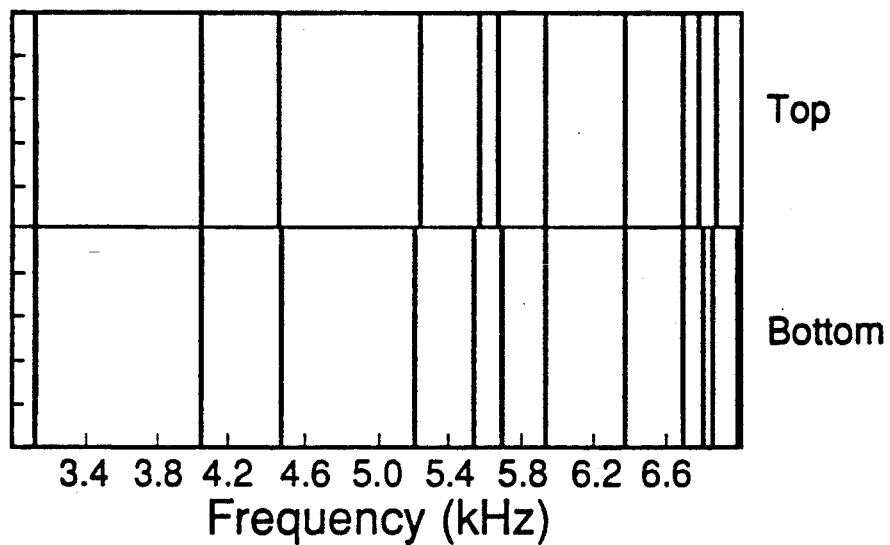
FIG. 8 illustrates the spectrum of mechanical resonances for $Ni_{80}P_{20}$ measured at 300 K. (bottom half) and the spectrum calculated from assumed values for the two elastic moduli (top half).
Figure 9:
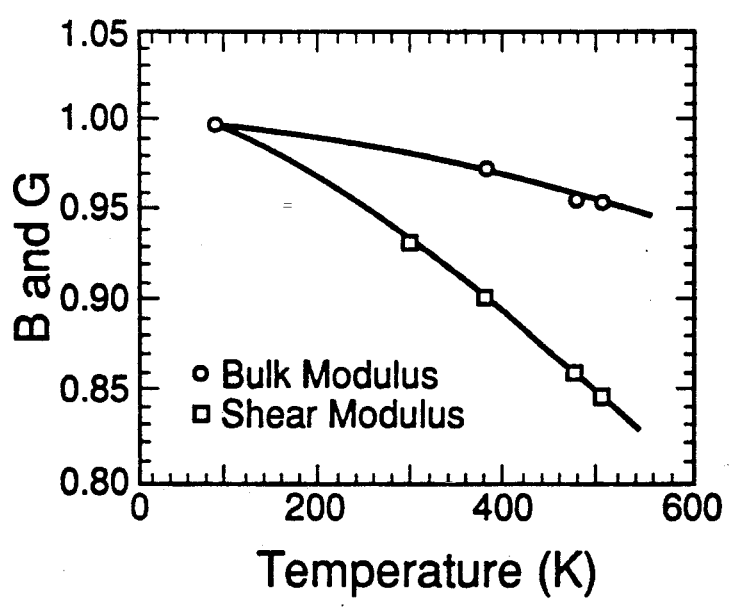
FIG. 9 graphically depicts the bulk and shear modulus of a Ni alloy measured as a function of temperature.

FIGS. 7(a) and 7(b) show the functions $P(\omega)$ and $P^2(\omega)$, plotted using the numerical values deduced for A, $\omega_r$, and $\Gamma$ from the fit shown in FIG. 6. A set of resonance and power curves illustrated by FIGS. 7A and 7B were obtained for each sample. FIG. 8 (bottom half) shows the measured spectrum of mechanical resonances in the $Ni_{80}P_{20}$ specimen at room temperature. The top half of FIG. 8 shows the theoretical spectrum calculated by the numerical procedure described in U.S. Pat. No. 4,976,148 by Migliori et al., incorporated herein by reference. While the calculated spectrum has one more resonance peak at about 592 kHz than the measured spectrum, this has no effect on the accuracy of the determination of elastic constants. The number of resonance frequencies in the spectrum greatly exceeds the number of frequencies needed to determine the elastic constants. FIG. 9 further shows the calculated bulk (B) modulus and shear ($\mu$) modulus for the amorphous sample of $Ni_{80}P_{20}$ over a wide temperature range to illustrate the capabilities of the present invention.

The system hereinabove described measures the mechanical resonance frequencies of the composite sample plus thin film. However, the relative contributions of the material sample and the magnetostrictive film to the elastic moduli of the composite sample are proportional to the ratio of the material thicknesses. For the 2.0 mm sample coated with a 15 $\mu$m thick film, discussed above, this ratio is 2000/15. Further, the Young's modulus of amorphous $Ni_{80}P_{20}$ is about one half that of nickel, reducing the error in the determination of the Young's modulus to about 0.15%. This error could be further reduced by using thinner magnetostrictive films. Films as thin as 5 $\mu$m thick have been used without a significant decrease in the signal-to-noise ratio.

It will be appreciated that the above resonance determinations are obtained without any mechanical contact between the sample and the surrounding structure. Frequency shifts are not induced by contact with mechanical transducers and resonant frequencies from the transducer structure are not introduced into the spectrum of measured resonance frequencies. Further, the orientation of the sample within the exciting coil structure is arbitrary so that the sample can be removed and replaced in the measuring system with a repeatable output.

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A resonance excitation system for remotely determining the resonance spectrum of a material sample, where the resonance spectrum is input to the rectangular parallelepiped resonance (RPR) method for determining material elastic moduli, comprising:
   a material sample having magnetostrictive properties;
   excitation coil means for exciting said sample with an oscillating magnetic field over a frequency range selected to include resonance frequencies within said resonance spectrum of said material sample; and
   detection coil means coaxial with said exciting coil means and adapted for axially mounting said material sample therein to detect the response of said material sample to said oscillating magnetic field.

2. A resonance excitation system according to claim 1, wherein said detection coil includes:
   a first coil wound in a first sense for axially receiving said sample and outputting a first signal; and
   a second coil coaxial with said first coil and wound in a second sense for outputting a second signal effective to combine with said first signal to improve the signal-to-noise ratio of said first signal.

3. A resonance excitation system according to claim 2, further including sample holder means coaxial with said exciting coil and said detection coil means for axially locating said sample within said first coil to maximize said signal-to-noise ratio.

4. A resonance excitation system according to claim 1, wherein said material sample is a rectangular parallelepiped of a non-magnetostrictive material with a magnetostrictive film deposited on at least one side.

5. A resonance excitation system according to claim 4, wherein said film of magnetostrictive material is deposited on three mutually orthogonal sides.

6. A resonance excitation system according to claim 1, wherein said means for exciting said sample includes:
   means for generating a sinusoidal excitation signal at a first frequency; and
   means for modulating said sinusoidal excitation frequency at a modulating frequency substantially less than said first frequency to generate a sample excitation signal that alternates about a linearly increasing average frequency.

7. A method for determining the resonance frequency spectrum of a material sample, where the material resonance frequencies are input to the RPR method for determining material elastic moduli, comprising the steps of:
   providing a material sample with magnetostrictive properties;
   generating about said material sample an oscillating magnetic field effective to excite said magnetostrictive properties to produce mechanical resonance in said sample material over a frequency range including said resonant frequency spectrum; and
   magnetically detecting a change of said magnetostrictive properties of said sample in a first coil and generating an output signal effective to identify the resonance responses of said sample to said exciting magnetic field.

8. A method according to claim 7, further including the step of preparing a magnetostrictive sample by depositing a thin film of magnetostrictive material on at least one area of a non-magnetostrictive sample material.

9. A method according to claim 7, wherein the step of exciting said sample further includes the steps of:
   generating a sinusoidal exciting signal at a linearly increasing frequency; and
   modulating said sinusoidal signal with a triangular signal effective to combine with said sinusoidal signal to generate an output signal having a frequency that alternates about a linearly increasing average frequency.

10. A method according to claim 7, wherein said step of detecting said sample response further includes the steps of:

detecting in a second coil coaxial with said first coil and axially removed from said sample said signal exciting said sample;

coaxially locating said first and second coils within said exciting signal to maximize the signal-to-noise ratio of said output signal from said first coil; and placing said sample within said first coil at an axial location effective to maximize said output signal.

* * * * *